United States Patent [19]
Cook et al.

[11] Patent Number: 5,428,072
[45] Date of Patent: Jun. 27, 1995

[54] METHOD OF INCREASING THE EFFICIENCY OF FEED CONVERSION IN ANIMALS

[75] Inventors: Mark E. Cook; Michael W. Pariza, both of Madison, Wis.

[73] Assignee: Wisconsin Alumni Research Foundation, Madison, Wis.

[21] Appl. No.: 7,413

[22] Filed: Jan. 22, 1993

Related U.S. Application Data

[63] Continuation-in-part of Ser. No. 875,896, Apr. 29, 1992.

[51] Int. Cl.$^6$ .............................................. A61K 31/20
[52] U.S. Cl. .................................................... 514/560
[58] Field of Search ................................. 514/560, 558

[56] References Cited

U.S. PATENT DOCUMENTS

| | | | |
|---|---|---|---|
| 4,603,142 | 7/1986 | Burger et al. | 514/456 |
| 4,868,001 | 9/1989 | Maruta | 426/623 |
| 5,017,614 | 5/1991 | Pariza et al. | 514/558 |
| 5,070,104 | 12/1991 | Pariza et al. | 514/549 |
| 5,162,337 | 11/1992 | Elbrecht et al. | 514/300 |

FOREIGN PATENT DOCUMENTS 294982  9/1986  Japan .................................. 514/560

OTHER PUBLICATIONS

Y. L. Ha; N. K. Grimm and M. W. Pariza, *Carcinogenesis*, vol. 8, No. 12, pp. 1881–1887 (1987).
Y. L. Ha; N. K. Grimm and M. W. Pariza, J. Agric. Food Chem., vol. 37, No. 1, pp. 75–81 (1987).
M. W. Pariza, Food Research Institute 1988 Annual Fall Meeting, Oct. 12, 1988.
The Merck Index, Tenth Edition (1983), p. 790.
The Merck Veterinary Manual, Fifth Edition (1979), pp. 1340–1343 and 1374 to 1379.

*Primary Examiner*—Marianne M. Cintins
*Assistant Examiner*—K. Weddington
*Attorney, Agent, or Firm*—Quarles & Brady

[57] ABSTRACT

A method of enhancing weight gain and feed efficiency in an animal which comprises administering to the animal a safe and effective amount of a conjugated linoleic acid.

4 Claims, No Drawings

METHOD OF INCREASING THE EFFICIENCY OF FEED CONVERSION IN ANIMALS

RELATED CASE

The present application is a continuation-in-part of our earlier application U.S. Ser. No. 07/875,896, filed Apr. 29, 1992.

FIELD OF THE INVENTION

The present invention generally relates to animal nutrition. More particularly, it relates to a method of increasing the efficiency of feed conversion in an animal into body weight.

BACKGROUND OF THE INVENTION

The efficiency of feed conversion into body weight varies significantly among different species of animals. Because feed is a relatively expensive cost factor in the production of food producing animals (50 to 70% of the cost of production), any improvement in the ability of the animal to convert feed into food products can directly improve the profitability of a food producer. For example, an increase in the efficiency of feed conversion in broilers that results in a 1% increase in body weight for the same amount of feed could alone result in savings of over 85 million dollars for the U.S. broiler industry. In addition, there would be millions of dollars of savings because of reduced mortality and a reduction in the days required before marketing the broilers.

There is a need for a method of improving the ability of healthy meat animals to more efficiently convert their feed to body weight or other edible products.

There also is a need for a safe and effective method for increasing the body weight of animals, including humans, who for medical or other reasons can only consume a limited amount of food.

BRIEF SUMMARY OF THE INVENTION

It is an object of the present invention to disclose a method of enhancing weight gain and feed efficiency in an animal.

We have discovered a method of enhancing weight gain and feed efficiency in an animal which comprises administering to said animal a weight gain enhancing and feed efficiency enhancing amount of a conjugated linoleic acid (CLA) selected from 9,11-octadecadienoic acid; 10,12-octadecadienoic acid; and mixtures thereof.

It will be apparent to those skilled in the art that the forementioned objects and other advantages may be achieved by the practice of the present invention.

DESCRIPTION OF THE PREFERRED EMBODIMENT

In a preferred embodiment of the method of the present invention the safe and effective amount of the conjugated linoleic acid, which is selected from 9,11-octadecadienoic acid; 10,12-octadecadienoic acid and mixtures thereof, is added to the feed of an animal in which it is desired to enhance the efficiency of feed conversion and enhance body weight. The amount of the conjugated linoleic acid to be added to the animal's feed will vary with the species and size of the animal. However, since the conjugated linoleic acids are natural food ingredients and relatively non-toxic, the amount which can be administered is not critical as long as it is enough to be effective.

The practice of the present invention is further illustrated by the examples which follow:

EXAMPLE 1

Groups of one week old chicks were fed a standard control diet, or the diet supplemented with 0.5% CLA, or with 0.5% linoleic acid. Feed consumption and weight gain were closely monitored. After 1 week, the feed conversion (grams of feed required to produce 1 gram increase in weight gain) were as follows: group fed control diet, 1.55 grams feed; group fed diet containing 0.5% CLA, 1.42 grams feed; group fed diet containing 0.5% linoleic acid, 1.56 grams feed. After 2 weeks, the feed conversions were: control group, 1.57 grams feed; group fed 0.5% CLA, 1.46 grams feed; group fed 0.5% linoleic acid, 1.53 grams feed. Clearly, when CLA was added to the diet, less feed was required to produce an equivalent weight gain. Hence, the CLA clearly improved the feed conversion efficiency of the animals.

EXAMPLE 2

Four pens of 10 chicks were fed a standard poultry ration with 0.5% lard (controls) or with 0.5% CLA mixed daily (2 pens per treatment). When the chicks were 3 weeks of age, they were weighed and then injected with endotoxin. As seen in Table 1 the chicks fed the unsupplemented diet failed to gain body weight over the next 24 hours, whereas the chicks fed CLA gained up to 10 grams ($p<0.07$).

TABLE 1

| Treatment | Av. Initial Wt. | Av. Wt. 24 h post endotoxin | Av. initial 24 h | % with no or negative gain |
|---|---|---|---|---|
| Control | 311 ± 12 | 311 ± 12 | 0 ± 3 | 53 |
| .5% CLA | 305 ± 9 | 315 ± 9 | 10 ± 4 | 27 |

EXAMPLE 3

Another group of chicks were fed a diet containing 0.5% CLA which was mixed with the feed daily. At 3 weeks of age the chicks were inoculated i.p. with 750 µg E. Coli 055:B5 endotoxin to stimulate immunity or phosphate buffered saline (PBS) as a control. The control chicks injected with PBS gained 9 g over the following 24 h period, and the CLA fed, PBS injected chicks gained 13.5 g. When chicks fed the control diet were injected with endotoxin, they lost 1.3 g of body weight over the following 24 h period. However, the CLA fed chicks even after endotoxin injection continued to gain an average of 6.6 g.

The results of the examples demonstrate that a lower proportion of chicks lose weight, within 24 hours of being injected with endotoxin, when the chicks ingest feed which contains CLA. In fact, the results in Tables 2 and 3 show that not only do a fewer number of birds lose weight but that those birds that are fed CLA actually gain considerably more weight than the control birds. In addition, in other studies the loss of body weight in rats fed CLA following stimulation was found to be only 50% of those not fed CLA.

TABLE 2

Effect of feeding different levels of CLA to chicks[1] on 24 hour body weight gain following endotoxin injection

| | 24 hr gain (g) | % neg. gain[3] |
|---|---|---|
| Diet | | |
| Control[2] | 1.7 | 40% |

TABLE 2-continued

Effect of feeding different levels of CLA to chicks[1] on 24 hour body weight gain following endotoxin injection

| | 24 hr gain (g) | % neg. gain[3] |
|---|---|---|
| 0.3% | 5.5 | 18% |
| 1.0% | 3.3 | 28% |
| Total CLA | | |
| − | 1.7 | 40% |
| + | 4.4 | 23% |

[1]Chicks were fed CLA for 14 consecutive days prior to endotoxin injection.
[2]Diet analysis revealed trace amounts of CLA in control diet. Contamination was most likely from pig lard which was used as the dietary fat source.
[3]The number of chicks with a negative weight gain during the 24 hour period immediately following endotoxin challenge.

TABLE 3

Effect of feeding CLA[1] to chicks for 3 or less days, or for more than 3 or more days[2] prior to endotoxin challenge on 24 hour body weight gain.

| Time fed CLA | Gain 24 hr post challenge | % BW change | Feed consumed per chick[3] |
|---|---|---|---|
| >3 days | −0.95 | −0.32 | 13.17 g |
| ≦3 days | −5.42 | −2.08 | 9.56 g |

[1]Chicks were fed 0.5% CLA in their diets.
[2]Greater than 3 days means up to 21 days.
[3]Feed consumed in the 24 hours post endotoxin challenge. Increased feed intake in this experiment equates with mitigation of illness from endotoxin challenge.

EXAMPLE 4

A group of seven rats was fed a semi-purified diet containing 5% corn oil and 0.5% stearic acid; a second group was fed the same diet with corn oil but also containing added free linoleic acid (0.5%). Three weeks later the animals were weighed. Four animals from each group were inoculated with endotoxin (1 mg/kg body weight); the remaining three animals from each group were inoculated with PBS. Rats fed the control diet and injected with PBS gained 7.4 g. Rats fed the diet to which linoleic acid had been added, and injected with PBS, gained 7.2 g. Rats fed control diet and injected with endotoxin lost 21.05 g. Rats fed diet to which linoleic acid had been added, and injected with endotoxin, lost only 11.4 g. These results are due to the conversion of added linoleic acid to CLA within the body of rats.

EXAMPLE 5

To demonstrate the unique ability of CLA to increase the efficiency of rabbits to convert feed into body weight, the rabbits were fed food supplemented with CLA, linoleic acid, and oils. The amounts of the CLA, the linoleic acid and the oils administered and the results are shown in Tables 4 to 6.

TABLE 4

SEMI-SYNTHETIC DIET WITH 12% COCONUT OIL AND 2% CORN OIL

| # | Food Consumption (g) | Body Weight Gain (g) | | | |
|---|---|---|---|---|---|
| 1 | 53 | | −60 | | |
| 2 | 48 | | −180 | | |
| 3 | 29 | | −150 | | |
| 4 | 59 | | −230 | | |
| 5 | 42 | } 46 g | −320 | } −200 g | |
| 6 | 60 | } (average) | −150 | } (average) | |
| 7 | 44 | | −330 | | |
| 8 | 37 | | −100 | | |
| 9 | 36 | | −210 | | |

TABLE 4-continued

SEMI-SYNTHETIC DIET WITH 12% COCONUT OIL AND 2% CORN OIL

| # | Food Consumption (g) | Body Weight Gain (g) |
|---|---|---|
| 10 | 47 | −270 |

TABLE 5

RABBITS #1-6 SWITCHED TO SAME SEMI-SYNTHETIC DIET SUPPLEMENTED WITH 0.5% COCONUT OIL

| # | Food Consumption (g) | | Body Weight Gain (g) | |
|---|---|---|---|---|
| 1 | 54 | | 0 | |
| 2 | 46 | | −100 | |
| 3 | 45 | } 53 g | −140 | } 105 g |
| 4 | 64 | } (average) | −120 | } (average) |
| 5 | 51 | | −170 | |
| 6 | 54 | | −100 | |

TABLE 6

RABBITS #7-10 SWITCHED TO SAME SEMI-SYNTHETIC DIET SUPPLEMENTED WITH 0.5% CLA

| # | Food Consumption (g) | | Body Weight Gain (g) | |
|---|---|---|---|---|
| 7 | 53 | | +30 | |
| 8 | 47 | } 49 g | +30 | } +30 g |
| 9 | 42 | } (average) | +50 | } (average) |
| 10 | 55 | | +10 | |

EXAMPLE 6

Three groups of rabbits (4/group) were fed control chow diet, chow diet containing 1% CLA, or chow diet containing 1% linoleic acid. The animals were given 100 g of feed each day. During a 3-week period, the mean weight gain for these groups was as follows:

| Rabbits fed control diet | 35 g |
|---|---|
| Rabbits fed diet containing 1% CLA | 132 g |
| Rabbits fed diet containing 1% linoleic acid | 75 g |

Clearly, the results show that CLA has a substantial positive effect on weight gain in these animals. The effect of CLA is greater than that observed with linoleic acid. During the 21-day time period, the CLA-fed rabbits ate 21 g CLA. Even if all of this CLA were retained as body fat, it would not account for the observed weight gain relative to controls (132 g−35g=97g).

EXAMPLE 7

Three groups of 14 healthy chicks were fed a basal diet with 0 (control), 0.3, or 1% CLA. Pen feed conversion was determined weekly for 3 weeks. During all periods, 0 to weeks, 0 to 2 weeks, 0 to 3 weeks of age on the dietary treatments, chicks fed CLA had marked improvements in the grams of feed needed to generate a gram of body weight (Table 7). The results in Table 7 are similar to the results seen in rats, mice and rabbits.

TABLE 7

| | Feed intake (g)/Body weight gain (g) | |
|---|---|---|
| Treatment | 0–1 wk | 0–2 wk |
| control | 2.53 | 2.62 |
| .3% CLA | 2.38 | 2.40 |
| 1% CLA | 2.34 | 2.16 |

EXAMPLE 8

Rats (7 per treatment) were individually caged and fed a diet containing 0.5% stearic acid, or 0.5% CLA for 4 weeks. Each week the amount (grams) of feed needed for gain (grams) was determined. Rats fed CLA consistently had better feed conversion than rats fed stearic acid (Table 8).

TABLE 8

| | Feed intake (g)/Body weight gain (g) | | | |
|---|---|---|---|---|
| Treatment | Wk 1 | Wk 2 | Wk 3 | Wk 4 |
| .5% stearate | 2.98 | 2.90 | 3.34 | 3.57 |
| .5% CLA | 2.51 | 2.49 | 3.02 | 3.36 |

EXAMPLE 9

Ten rats, individually caged, were fed a control diet (0.5% stearate) or a diet containing 0.5% CLA for 1 week, weeks, 3 weeks, or 4 weeks. Feed intake/gain was calculated for each period rats were fed CLA or stearate. Table 9 shows that rats fed CLA for 2, 3, or 4 weeks had a marked improvement in the grams of feed needed for a gram of gain.

TABLE 9

| | Feed intake (g)/Body weight gain (g) | | | |
|---|---|---|---|---|
| Treatment | Wk 1* | Wk 2 | Wk 3 | Wk 4 |
| .5% stearate | 1.87 | 2.13 | 2.48 | 2.73 |
| .5% CLA | 1.85 | 1.58 | 2.11 | 2.64 |

*indicates the length of time the rats were fed CLA.

EXAMPLE 10

Fourteen individually caged rats were assigned to each of 3 dietary treatments: Control (no CLA), 0.3% CLA, and 1% CLA. The amount of feed (grams) needed for each gram of gain was determined each week for 2 weeks. Rats fed 0.3 or 1% CLA had a reduction in the grams of feed needed for each gram of gain (Table 10).

TABLE 10

| | Feed intake (g)/Body weight gain (g) | | |
|---|---|---|---|
| % CLA | 0–1 Wk | 1–2 Wk | 0–2 Wk |
| 0 | 2.74 | 2.68 | 2.71 |
| .3 | 2.27 | 2.17 | 2.21 |
| 1.0 | 1.89 | 2.20 | 2.05 |

EXAMPLE 11

Three-week old mixed sexed mice (5 groups of 4 mice per dietary treatment) were fed a diet containing no fatty acid addition, 0.5% fish menhaden oil, or 0.5% CLA. After 15 days of feeding 2 groups of mice per dietary treatment were injected ip with 1 mg *E. coli* O55:B5 lipopolysaccharide (LPS) in HEPES buffer, 1 group of mice per dietary treatment was injected ip with mouse interleukin-1 in HEPES buffer, and 2 groups of mice per dietary treatment were injected ip with only HEPES buffer. The percent change in feed consumed of mice injected with LPS or IL-1 relative to the HEPES injected mice within each dietary treatment was determined hours after the injections. Table 11 shows that CLA-fed mice injected with LPS had less of a relative reduction in feed intake than mice fed fish oil or no fat inclusion. When the mice fed the various dietary treatments were injected with IL-1, those mice fed the basal diet had a 20% relative reduction in feed intake, while those fed CLA had an actual 10% increase in relative feed intake. The fish oil fed mice had intermediate intakes. These data suggest that CLA is effective in preventing or reducing the negative effects immune stimulation has on feed intake.

TABLE 11

| Consumption (24 hr) following immune stim. (% gain relative to HEPES injection) | | |
|---|---|---|
| Treatment | IL-1 | LPS |
| Basal | −20.0 | −96.3 |
| .5% fish oil | +4.5 | −95.1 |
| .5% CLA | +10.3 | −27.5 |

The use of CLA in poultry feed improves the ability to convert feed, enhances growth and prevents weight loss in poultry. For broiler chickens alone, a decrease in feed/body weight of 0.01 could equal savings of $22 million/yr to the broiler industry. The difference between the conversion of the control and 1% CLA would thus be worth over $1 billion/yr.

In another embodiment of the invention, linoleic acid is administered to an animal which can convert the linoleic acid into CLA or which modulates the level of CLA in the body of an animal or a human. The linoleic acid is converted to CLA in the animal, probably by microorganisms in the animal's gastrointestinal system (S. F. Chin, W. Liu, K. Albright, and M. W. Pariza, 1992, FASEB J. 6:Abstract #2665).

The method of the present invention may take other embodiments. For example, the CLA can be administered to an animal in a pharmaceutical or veterinary composition, such as tablets, capsules, solutions or emulsions, containing a safe and effective dose of the CLA.

The animal feeds and pharmaceutical preparations for use in the method of the present invention are those containing the active forms of the free conjugated linoleic acids (CLA), especially 9,11-octadecadienoic acid and 10,12-octadecadienoic acid or mixtures thereof in combination with a conventional animal feed (e.g. poultry feed), human food supplement, or an approved pharmaceutical diluent.

The active forms of CLA include, in addition to the free acids the active isomers of CLA; non-toxic salts thereof; active esters and other active chemical derivatives thereof; and mixtures thereof.

The free conjugated linoleic acids (CLA) have been previously isolated from fried meats and described as anticarcinogens by Y. L. Ha, N. K. Grimm and M. W. Pariza, in Carcinogenesis Vol. 8, No. 12, pp. 1881–1887 (1987). Since then, they have been found in some processed cheese products. Y. L. Ha, N. K. Grimm and M. W. Pariza, in J. Agric. Food Chem., Vol. 37, No. 1, pp. 75–81 (1987). However, animal feeds containing CLA, or its non-toxic derivatives, such as the sodium and potassium salts, as an additive in combination with conventional animal feeds or human foods are believed to be novel.

The free acid forms of the CLA may be prepared by isomerizing linoleic acid. The non-toxic salts of the free CLA acids may be made by reacting the free acids with a non-toxic base. Natural CLA may also be prepared from linoleic acid by the action an isomerase from a harmless microorganism such as the Rumen bacterium *Butyrivibrio fibrisolvens*. Harmless microorganisms in the intestinal tracts of rats and other monogastric animals may also convert linoleic acid to CLA (S. F. Chin, W. Liu, K. Albright and M. W. Pariza, 1992, FASEB J.6:Abstract #2665).

The CLA obtained by the practice of the described methods of preparation contains one or more of the 9,11-octadecadienoic acids and/or 10,12-octadecadienoic acids and active isomers thereof. It may be free or bound chemically through ester linkages. The CLA is heat stable and can be used as is, or dried and powdered. The CLA is readily converted into a non-toxic salt, such as the sodium or potassium salt, by reacting chemically equivalent amounts of the free acid with an alkali hydroxide at a pH of about 8 to 9.

Theoretically, 8 possible geometric isomers of 9,11- and 10,12-octadecadienoic acid (c9,c11; c9,t11; t9,c11; t9,t11; c10,c12; c10,t12; t10,c12 and t10,t12) would form from the isomerization of c9,c12-octadecadienoic acid. As a result of the isomerization, only four isomers (c9,c11; c9,t11; t10,c12; and c10,c12) would be expected. However, of the four isomers, c9,t11- and t10,c12- isomers are predominantly produced during the autoxidation or alkali-isomerization of c9,c12-linoleic acid due to the co-planar characteristics of 5 carbon atoms around a conjugated double-bond and spatial conflict of the resonance radical. The remaining two c,c-isomers are minor contributors.

The relatively higher distribution of the t,t-isomers of 9,11- or 10,12-octadecadienoic acid apparently results from the further stabilization of c9,t11- or t10,c12-geometric isomers, which is thermodynamically preferred, during an extended processing time or long aging period. Additionally the t,t-isomer of 9,11- or 10,12-octadecadienoic acid that was predominantly formed during the isomerization of linoleic acid geometrical isomers (t9,t12-, c9,t12- and t9,c12-octadecadienoic acid) may influence the final ratio of the isomers or the final CLA content in the samples.

Linoleic acid geometrical isomers also influence the distribution of minor contributors (c,c-isomers of 9,11- and 10,12-, t9,c11- and c11,t12-octadecadienoic acids). The 11,13-isomer might be produced as a minor product from c9,c12-octadecadienoic acid or from its isomeric forms during processing.

The exact amount of CLA to be administered, of course, depends upon the animal, the form of CLA employed, the route of administration, and extent of the increase in body weight desired.

Generally, the amount employed of CLA and its non-toxic salts employed as a pharmaceutical for humans will range from about 1,000 parts per million (ppm) to about 10,000 ppm of CLA of the human's diet. However, the upper limit of the amount to be employed is not critical because CLA is relatively non-toxic and it is a normal constituent of the human diet (including human breast milk).

The preferred pharmaceutical and veterinary compositions of CLA contain the non-toxic sodium or potassium salt of CLA in combination with a pharmaceutical diluent. When the compositions are solutions or suspensions intended for oral administration the diluent will be one or more diluents, such as lactose or starch, and the product will be a tablet, capsule or liquid. When the compositions are solutions or suspensions intended for parenteral administration the preferred diluent will be Sterile Water for Injection U.S.P.

The amount of CLA to be added to an animal's feed as an additive can range from 0.01% to 2.0% or more by weight of the animal's or human's food.

It will be readily apparent to those skilled in the art that a number of modifications or changes may be made without departing from the spirit and scope of the present invention. Therefore, the invention is only to be limited by the claims.

We claim:

1. A method of increasing the efficiency of feed conversion to body weight in an animal which comprises administering orally or parenterally to said animal a safe amount of a member selected from the group consisting of 9,11 octadecadienoic acid, 10,12-octadecadienoic acid and non-toxic salts thereof which is effective to increase the efficiency of feed conversion to body weight in the animal.

2. A method of claim 1 in which the animal is a bird.

3. A method of claim 1 in which the animal is a mammal.

4. A method of modifying an animal food to increase the ability of the animal food to increase the efficiency of the conversion of the food to body weight in an animal, said method comprising adding to said animal food a safe amount of a conjugated linoleic acid selected from the group consisting of 9,11-octadecadienoic acid, 10,12-octadecadienoic acid, and mixtures thereof, said amount being effective to increase the efficiency of food conversion in the animal.

* * * * *